United States Patent [19]

Boog et al.

[11] Patent Number: 5,789,212
[45] Date of Patent: Aug. 4, 1998

[54] PROCESS FOR PRODUCING GAMMA-LACTOMES

[75] Inventors: Arnoldus L. G. M. Boog, Bussum; Adrianus M. van Grinsven, Oss; Alfons L. J. Peters; Robert Roos, both of Bussum; Andras J. Wieg, Amsterdam, all of Netherlands

[73] Assignee: Unilever Patent Holdings B.V., Rotterdam, Netherlands

[21] Appl. No.: 447,498

[22] Filed: May 23, 1995

Related U.S. Application Data

[63] Continuation of Ser. No. 443,947, Dec. 1, 1989, abandoned.

[30] Foreign Application Priority Data

Dec. 1, 1988 [EP] European Pat. Off. ............ 88202754

[51] Int. Cl.$^6$ .................. C12P 7/62; C12P 7/64
[52] U.S. Cl. .................. 435/135; 435/134; 435/146; 435/126
[58] Field of Search .................. 435/134, 135, 435/146, 126

[56] References Cited

U.S. PATENT DOCUMENTS

| 3,076,750 | 2/1963 | Muys et al. | 435/136 |
| 4,560,656 | 12/1985 | Farbood et al. | 435/134 |

FOREIGN PATENT DOCUMENTS

| 0258993 | 3/1988 | European Pat. Off. | C12P 7/42 |
| 60-66991 | 4/1985 | Japan . | |
| 60-100508 | 6/1985 | Japan . | |
| 8301072 | 3/1983 | WIPO | C12P 7/42 |

OTHER PUBLICATIONS

Patent Abstracts of Japan, vol. 9, No. 241, Sep. 27, 1985; and No. 196, Aug. 13, 1985.

Okuyame et al., Production of Castor Oil Having Improved Quality.

Okuyama et al., Cosmetics.

*Primary Examiner*—Leon B. Lankford, Jr.
*Attorney, Agent, or Firm*—Pillsbury Madison & Sutro LLP

[57] ABSTRACT

The invention provides a process for producing gamma-lactones useful for incorporation in flavorings and fragrances, wherein a micro-organism which is acceptable for making food grade products and which does not metabolize gamma-lactones, is cultured aerobically in a culture medium containing as the substrate a hydroxy fatty acid having an even number 4 of carbon atoms between the carboxyl group and the carbon atom carrying the hydroxy group. The preferred micro-organism is a *Saccharomyces cerevisiae*, *Debaromyces hansenii* or *Candida boidinii* species. The gamma-hydroxy-alkanoic acid reaction product of the process is lactonized either in the fermentation broth or after separation therefrom. Especially suitable are 12-hydroxy fatty acids such as ricinoleic acid. The hydroxy fatty acid may be added either pure or as the mixture obtained by hydrolysis of an ester thereof. Enzymatic hydrolysis of such ester may be done in situ in the fermentation broth.

5 Claims, No Drawings

PROCESS FOR PRODUCING GAMMA-LACTOMES

This is a continuation of application Ser. No. 07/443,947, filed on Dec. 1, 1989, which is abandoned.

The invention concerns a process for producing gamma-hydroxy alkanoic acid from hydroxy fatty acids having an even number 4 of carbon atoms between the carboxyl group and the carbon atoms carrying the hydroxyl group through microbial fermentation, and the subsequent transformation of these gamma-hydroxy-alkanoic acids into gamma-lactones.

Several gamma-lactones are widely used by the flavour and fragrance industry for improving the organoleptic qualities of flavourings and perfumes. For their application in flavourings it is considered advantageous to produce these lactones from natural raw materials in a process which is also considered natural. Microbial fermentation is such a process.

The preparation of gamma-hydroxy-decanoic acid and subsequently of gamma-decalactone from castor oil or castor oil hydrolysate with specific microorganisms is disclosed in U.S. Pat. No. 4,560,656 and references cited therein. In EP-A-0258993 it is disclosed how to use ricinoleic acid as the substrate and other microorganisms are specified.

However, the microorganisms mentioned in the prior art are not generally recognized as "food grade". Moreover, there is a need for processes producing higher quantities of lactones than most of those described in the prior art.

In Japanese Kokai 60-066991 and 60-100508 it is disclosed how to improve the quality of castor oil which is contaminated with small quantities of ricinoleic acid by subjecting it to a fermentative treatment with e.g. *Saccharomyces cerevisiae, Pichia farinosa, Candida utilis, Hansenula anomala* or other microorganisms. Castor oil thus treated is said to be more suitable for cosmetic purposes owing to an improvement of the spreadability and the feel on the skin and owing to an improvement of the odour to milky and cream-like. These improvements are ascribed to the removal of ricinoleic acid and the formation of minute quantities of gamma-decalactone. However, inspection of the examples of these patent applications reveals that, although a small amount of gamma-decalactone is formed, the amount of ricinoleic acid is actually higher after than before the fermentative treatment. The amount of gamma-decalactone formed in this process is in the order of 1.5% based on the amount of ricinoleic acid, 400 ppm. based on the amount of castor oil and 0.015 g per kg of fermentation broth. Thus, the process described in these Japanese patent applications is clearly not suitable for the production of gamma-decalactone on an industrial scale.

A process was found for producing gamma-lactones using a micro-organism cultured in a culture medium containing a suitable substrate for producing gamma-hydroxy-alkanoic acids, wherein a microorganism which is generally considered acceptable for making food grade products and which does not, or only very slowly, metabolize gamma-lactones, is cultured aerobically in a culture medium containing a hydroxy fatty acid having an even number $\geq 4$ of carbon atoms between the carboxyl group and the carbon carrying the hydroxyl group, under such conditions and for a period of time sufficient to produce at least 0.1 g of gamma-hydroxy-alkanoic acid and/or gamma-lactone per kg of fermentation broth, followed by conversion of gamma-hydroxy-alkanoic acid to gamma-lactone at a pH below 7 and recovery of the gamma-lactone substantially free from the original hydroxy fatty acid. Preferably, the microorganism is a species chosen from the group consisting of *Saccharomyces cerevisiae, Debaromyces hansenii, Candida boidinii, Candida silvicola, Candida apicola, Zygosaccharomyces fermentati, Torulaspora delbruckii*. More preferably, the microorganism species is chosen from *Saccharomyces cerevisiae, Debaromyces hansenii* and *Candida boidinii*. Particularly useful are *Saccharomyces cerevisiae* species. The process is preferably carried out under such conditions as to produce at least 1 g of gamma-hydroxy acid/gamma-lactone per kg of fermentation broth.

The hydroxy fatty acid having an even number $\geq 4$ of carbon atoms between the carboxyl group and the carbon carrying the hydroxyl group, which is used as the substrate in the process of the invention, may be added to the culture medium in substantially pure form, but it may also be added as part of a mixture, e.g. a mixture obtained by hydrolysis of an ester of the hydroxy fatty acid. Especially suitable mixtures may be obtained by enzymatic hydrolysis of such esters. The enzymatic hydrolysis may be performed either before or after addition to the culture medium. In the latter case, a mixture of the ester and a suitable enzyme is added to the culture medium and hydrolysis takes place during the process of the invention, thereby preparing the hydroxy fatty acid substrate in situ. Some of the microorganisms used in this invention themselves produce lipase activity, in which case a hydroxy fatty acid glycerol ester may be used as the substrate without the addition of a separate enzyme.

The hydroxy fatty acids or their esters should preferably be derived from natural sources. Suitable esters found in nature are hydroxy fatty acid glycerides such as ricinoleic acid glyceride present in castor oil, and hydroxy fatty acid-carbohydrate esters such as found in Jalap resins. Also suitable are hydroxy fatty acids obtained through microbial conversion of non-hydroxy fatty acids, such as 10-hydroxy-stearic acid obtained from oleic acid.

Thus, a suitable starting material for the process of the invention is ricinoleic acid, either substantially pure or as present in the hydrolysis mixture of castor oil. Also suitable is dihydro-ricinoleic acid, which may be obtained by hydrolysis of hydrogenated castor oil. In these cases the process leads to the production of gamma-hydroxy-decanoic acid and ultimately to gamma-decalactone. Other suitable starting materials are 3,12-dihydroxy-palmitic acid and 3,12-dihydroxy-pentadecanoic acid, both obtainable from hydrolysed Jalap resin, which lead to gamma-octalactone and gamma-heptalactone, respectively. These hydroxy fatty acids all have in common that they contain 10 carbon atoms between the carboxyl group and the carbon atom carrying the hydroxyl group.

Suitable microorganism strains may be obtained from well-known sources, such as scientific culture collections or commercial sources. Examples of commercially available *Saccharomyces cerevisiae* strains are:

Kitzinger Reinhefe All purposes dry yeast
Kitzinger Reinhefe Samos
Kitzinger Reinhefe Steinberg
  Paul Arauner, W.Germany.
Fermipan instant yeast
Ferotin instant yeast
  Gist-Brocades, Delft, The Netherlands.
Champagne dry yeast
Rhine wine dry yeast
Sauternes dry yeast
Tokayer dry yeast
  Souplesse Import, The Netherlands.
Vierka wine yeast "Chablis"
  Friedrich Sauer, W. Germany.

Fleischmann active dry yeast
  Standard Brands Inc., New York, USA.
Wine yeast Broerken
  Liberty Nederland, The Netherlands.
Brewers yeast
  Propps, Sweden
Vinkwik wine yeast
  Jan Dekker, Wormerveer, The Netherlands.
Bakers yeast
  Bruggeman, Belgium.

The fermentation according to the invention is carried out at a pH between 3 and 9, preferably between 4.5 and 7.5, more preferably between 5 and 7.2. The temperature should be kept between 10° and 40° C., preferably between 15° and 35° C. Aeration is preferably regulated so as to keep $pO_2$ of the fermentation broth above 10% of saturation.

A suitable culture medium comprises usual nutrients, i.e. carbon sources, nitrogen sources, inorganic salts, growth factors and trace elements. Suitable carbon sources are known in the art and include saccharides and saccharide-derived polyols, glycerol, organic acids such as lactic acid, citric acid, succinic acid, ascorbic acid. Among the suitable nitrogen sources are: peptone, meat extract, yeast extract, corn steep liquor, amino acids. Well-balanced culture media preferably contain at least a small amount of yeast extract, which in most cases obviates the need to add vitamins, inorganic salts, trace elements and the like separately.

Particularly well-balanced culture media contain at least 0.1% w/w of yeast extract and 0.25% w/w or more of peptone. In some cases, the addition of up to 20 mg/kg of $Fe^{+2}$, e.g. as $FeSO_4$, may be advantageous. The culture medium is preferably inoculated with at least 1,000 cells/kg. The hydroxy fatty acid used as substrate may be conveniently added as the only carbon source, either at the start of the culture or at a later stage, e.g. when the maximum amount of cells has been reached. It may also be added gradually, either in a fed batch-type operation or e.g. by adding a hydroxy fatty acid ester and a suitable enzyme, e.g. a lipase, to the culture medium, causing the hydroxy fatty acid to be liberated gradually during the fermentation. The hydroxy fatty acid may also be added dissolved in a suitable organic solvent which is not toxic to the micro-organism, such as a mineral oil or a hydrocarbon, or, in case the micro-organism does not itself produce lipase activity, a glyceride oil of vegetable or animal origin Either way, a total amount of at least 0.1% and preferably more than 1% by weight of hydroxy fatty acid is added to the culture medium.

A level of 0.1 g gamma-lactone and gamma-hydroxy-alkanoic acid together per kg of fermentation broth is usually reached within 24–36 hours and the maximum amount will generally be reached within 10 days. In many cases this maximum will already be reached in a much shorter time. However, the exact fermentation time is not critical since, unlike fermentation processes of the prior art, in the process of the invention the gamma-lactone content does not or hardly diminish with time after reaching its maximum. Thus, the lactone is substantially stable in the fermentation broth.

If desired, the microorganism may be immobilised on a support employing a usual technique such as described in Eur. J. App. Mic. & Biotech 15 (1982), pp. 147–152 and Biotech & Bioeng 19 (1977), p. 387 et seq.

To facilitate the dispersion of the substrate in the culture medium, a suitable emulsifier may be added in an amount of up to 1% w/w of the culture medium. Foaming of the fermentation broth may be prevented by the addition of conventional anti-foaming agents.

The reaction product usually consists of a mixture of gamma-hydroxy-alkanoic acid and the corresponding gamma-lactone. This mixture may be separated from the fermentation broth with usual techniques, e.g. extraction with a suitable absorbent or with an organic solvent. When the hydroxy fatty acid substrate was added as a solution in an organic solvent, the reaction product will also be dissolved in that solvent and the solvent may simply be separated from the fermentation broth. Thereafter the gamma-hydroxy-alkanoic acid is converted to the gamma-lactone in the usual way at a pH below 7. Alternatively, lactonisation may first be completed in the fermentation broth by lowering the pH to below 7, preferably below 5 and mild application of heat, if necessary. The lactone may also be separated from the fermentation broth by extraction and purified, if desired, by distillation.

The lactones obtained by the process according to the invention may be added to flavourings or foodstuffs, either as such or dissolved in a suitable solvent or processed into a powdered product. Flavouring components which may be used with the lactones according to the invention are well known in the art and are mentioned, e.g., in S. Arctander, Perfume and Flavor Materials of Natural Origin (Elizabeth, N.J., USA, 1969) in T. E. Furia et al., CRC Fenaroli's Handbook of Flavor Ingredients, 2nd Ed. (Cleveland, CRC Press Inc., 1975) and in H. B. Heath, Source Book of Flavors (The Avi Publishing Company Inc., Westport, Conn., 1981).

The invention is illustrated by the following Examples but is not in any way limited thereto.

EXAMPLE 1

100 ml autoclaved (20 minutes at 120° C.) culture medium contained in a baffled flask and consisting of 2% w/w of peptone, 0.5% w/w of yeast extract and 3.2% w/w of castor oil hydrolysate Nouracid CS 80 (marketed by AKZO, Amersfoort, The Netherlands) was inoculated with $4.10^4$ cells of Saccharomyces cerevisiae (Kitzinger Reinhefe all purposes dry yeast). The pH of the culture medium was 6.5 and remained steady during the whole fermentation. The culture was incubated at 28° C. on a rotary straker (150 rpm) for 5 days.

Samples were periodically removed to determine the progress of the process. The concentration of gamma-decalactone was determined after acidification, extraction with ethyl acetate and separation of the layers, using GLC. After a lag phase of about 20 hours, the concentration of gamma-decalactone steadily increased up to the end of the fermentation. At the end of the fermentation, the broth was acidified to pH 3 with dilute sulphuric acid and extracted as above. The organic layer was separated and the solvent evaporated. The residue was distilled to provide the gamma-decalactone. In the fermentation broth 2.06 g/kg gamma-decalactone was obtained, representing a molar yield of about 13% on added ricinoleic acid in the castor oil hydrolysate. Since about 87% of the ricinoleic acid could be recovered from the broth, the fermentation yield is 100% based on metabolized ricinoleic acid.

EXAMPLE 2

A fermentation was carried out, using the procedures and materials described in Example 1, except that the Saccharomyces cerevisiae strain ATCC 24903 was used and 2.7% w/w of castor oil hydrolysate Nouracid CS 80 was added. 3.75 g/kg gamma-decalactone was obtained from the fermentation broth, representing a molar yield of about 30% based on added ricinoleic acid. Since about 70% of the ricinoleic acid could be recovered unchanged, the molar yield on metabolized ricinoleic acid was again 100%.

EXAMPLE 3

A fermentation was carried out, using Fermipan instant yeast of Gist-Brocades, Delft, The Netherlands, as the *Saccharomyces cerevisiae* strain and starting from 3.1% w/w of castor oil hydrolysate. Otherwise the procedures and materials described in Example 1 were used. 2.1 g/kg gamma-lactone was obtained from the fermentation broth.

EXAMPLE 4

Example 1 was repeated, except that 2.7% w/w of purified ricinoleic acid was added instead of castor oil hydrolysate. The same results as in Example 1 were obtained.

EXAMPLE 5

Example 1 was repeated, using, however, a mixture of 3.2% w/w of castor oil and 23 ppm/w of lipase L 1754 of Sigma Chemie GmbH, Deisenhofen, West-Germany, instead of castor oil hydrolysate. The same results as in Example 1 were obtained.

EXAMPLE 6

A fermentation was carried out in a 1 l fermentor (supplied by Applikon, Schiedam, The Netherlands), using 1 l of the culture medium described in Example 1, inoculated with $4 \times 10^5$ cells of Kitzinger Reinhefe All purposes dry yeast. During the fermentation, the pH remained around 6.5. The temperature was kept at 28° C., the airflow at 0.1 vvm and the stirring rate at 500 rpm. To avoid foaming of the fermentation broth, 100 ppm by weight of anti-foam emulsion M-10 (Dimethicone, Biesterveld, Alphen a/d Rijn, The Netherlands) was added at the start of the fermentation. The progress of the fermentation was followed as described in Example 1. After 5 days, the maximum amount of gamma-decalactone was reached. The broth was acidified to pH 3 and the lactone isolated as described in Example 1, yielding 2.5 g of gamma-decalactone.

EXAMPLE 7

Fermentations were carried out using the procedures and materials decribed in Example 1, but using the microorganism strains mentioned below in the table. The quantities of ricinoleic acid added (in % w/w) and of gamma-decalactone obtained (in g/kg) are given for each microorganism strain.

| Microorganism strain | ricinoleic acid | deca-lactone |
| --- | --- | --- |
| Zygosaccharomyces fermentati QI04420 | 4 | 0.54 |
| Candida boidinii QI10385 | 4 | 1.80 |
| Candida silvicola QI10393 | 4 | 0.60 |
| Candida silvicola QI10393 | 1 * | 0.17 |
| Candida apicola QI02267 | 4 | 0.62 |
| Torulaspora delbruckii QI01900 | 4 | 0.60 |

* In these case unhydrolysed castor oil was added as the substrate

We claim:

1. A process for producing gamma-deca lactone comprising aerobically culturing *Saccharomyces cerevisiae* in a culture medium containing more than 1% by weight of ricinoleic acid and which has been inoculated with at least 1000 cells of *Saccharomyces cerevisiae* per kg of culture medium at a pH between 3 and 9 and a temperature between 10° and 40° C. while aerating so that $pO_2$ of the culture medium is above 10% of saturation and continuing said culturing for at least 20 hours and sufficient to produce a total of at least 1 g of gamma-deca lactone, or a mixture thereof with gamma-hydroxy-decanoic acid per kg of fermentation broth in a period of not more than 5 days, converting gamma-hydroxy-decanoic acid if present to gamma-deca lactone at a pH below 7 in the fermentation broth or after separating the gamma-hydroxy-decanoic acid from the fermentation broth, and recovering the gamma-deca lactone substantially free from the original ricinoleic acid.

2. A process according to claim 1, wherein the ricinoleic acid is obtained by hydrolysis of castor oil.

3. A process according to claim 1, wherein the gamma-hydroxy-alkanoic acid is lactonized in the fermentation broth and the gamma-lactone is recovered.

4. A process for producing gamma-deca lactone comprising aerobically culturing *Saccharomyces cerevisiae* in a culture medium containing more than 1% by weight of ricinoleic acid and which has been inoculated with at least 1000 cells of *Saccharomyces cerevisiae* per kg of culture medium at a pH between 4.5 and 7.5 and a temperature between 10° and 40° C. while aerating, continuing said culturing to produce a total of at least 1 g of gamma-deca lactone per kg of fermentation broth in a period of not more than 5 days, and recovering the gamma-deca lactone substantially free from the original ricinoleic acid.

5. The process of claim 4 wherein the culturing is carried out at a pH of about 6.5.

* * * * *